(12) United States Patent
Zhai et al.

(10) Patent No.: US 11,661,594 B2
(45) Date of Patent: May 30, 2023

(54) MUTANT OF LYCOPENE EPSILON CYCLASE (LCYE) GENE CRUCIAL IN WHEAT CAROTENOID SYNTHESIS PATHWAY AND USE THEREOF

(71) Applicant: Crop Research Institute, Shandong Academy of Agricultural Sciences, Shandong (CN)

(72) Inventors: Shengnan Zhai, Shandong (CN); Jianjun Liu, Shandong (CN); Haosheng Li, Shandong (CN); Jianmin Song, Shandong (CN); Aifeng Liu, Shandong (CN); Xinyou Cao, Shandong (CN); Dungong Cheng, Shandong (CN); Zhendong Zhao, Shandong (CN); Cheng Liu, Shandong (CN); Jun Guo, Shandong (CN); Ran Han, Shandong (CN); Yan Zi, Shandong (CN); Faji Li, Shandong (CN); Xiaolu Wang, Shandong (CN)

(73) Assignee: Crop Research Institute, Shandong Academy of Agricultural Sciences, Shandong (CN)

( * ) Notice: Subject to any disclaimer, the term of this patent is extended or adjusted under 35 U.S.C. 154(b) by 130 days.

(21) Appl. No.: 17/194,735

(22) Filed: Mar. 8, 2021

(65) Prior Publication Data
US 2021/0355477 A1 Nov. 18, 2021

(30) Foreign Application Priority Data
Mar. 9, 2020 (CN) .......................... 202010156364.4

(51) Int. Cl.
*C12N 9/90* (2006.01)
*C12N 15/82* (2006.01)

(52) U.S. Cl.
CPC ............. *C12N 9/90* (2013.01); *C12N 15/825* (2013.01); *C12Y 505/01018* (2013.01)

(58) Field of Classification Search
CPC . C12N 9/90; C12N 15/825; C12Y 505/01018
See application file for complete search history.

(56) References Cited

PUBLICATIONS

Richaud et al. "Identification of Lycopene epsilon cyclase (LCYE) gene mutants to potentially increase β-carotene content in durum wheat (*Triticum turgidum* L.ssp. durum) through TILLING" 2018 PLOS One 13(12): e0208948, 17 total pages. (Year: 2018).*

(Continued)

*Primary Examiner* — Matthew R Keogh
*Assistant Examiner* — Rebecca Stephens
(74) *Attorney, Agent, or Firm* — Day Pitney LLP; Anthony A. Kassas (57) ABSTRACT

The present disclosure discloses a mutant of a lycopene epsilon cyclase (Lcye) gene crucial in a wheat carotenoid synthesis pathway and use thereof. The present disclosure provides the following proteins: (1) a protein obtained by substituting serine at position 253 of an Lcye-D1 protein with phenylalanine; (2) a derived protein that is obtained by subjecting the protein in (1) to substitution and/or deletion and/or addition of one or more amino acid residues and has the same ability as the protein in (1); (3) a protein that has a homology of more than 99%, more than 95%, more than 90%, more than 85%, or more than 80% with the amino acid sequence defined in any one of (1) and (2) and has the same function as the amino acid sequence; and (4) a fusion protein obtained by attaching a tag to N-terminus and/or C-terminus of the protein in any one of (1) to (3). The present disclosure not only verifies the function of an Lcye gene, but also provides a theoretical basis and a germplasm resource for improving the color character of flour and products thereof.

3 Claims, 2 Drawing Sheets

Specification includes a Sequence Listing.

(56) References Cited

PUBLICATIONS

Guo et al. "Development of a High-Efficient Mutation Resource with Phenotypic Variation in Hexapioid Winter Wheat and Identification of Novel Alleles in the TaAGP.L-B1 Gene" 2017 Front. Plant Sci. 8(1404): doi: 10.3389/fpls.2017.01404; 9 total pages. (Year: 2017).*

* cited by examiner

MUTANT OF LYCOPENE EPSILON CYCLASE (LCYE) GENE CRUCIAL IN WHEAT CAROTENOID SYNTHESIS PATHWAY AND USE THEREOF

CROSS-REFERENCE TO RELATED APPLICATIONS

This U.S. application Ser. No. 17/194,735, filed on Mar. 8, 2021, claims the benefit of priority to Chinese Patent Application No. 202010156364.4, filed on Mar. 9, 2020. The content of each of the above referenced patent applications is incorporated herein by reference in its entirety for any purpose whatsoever.

REFERENCE TO SEQUENCE LISTING

This U.S. application Ser. No. 17/194,735, filed on Mar. 8, 2021 incorporates herein by reference in its entirety for any purpose whatsoever the file titled "SEQUENCE LISTING" created on Mar. 10, 2021 having a size of 13,337 bytes.

TECHNICAL FIELD

The present disclosure relates to the field of biotechnology, and in particular to a mutant of a lycopene epsilon cyclase (Lcye) gene crucial in a wheat carotenoid synthesis pathway and use thereof.

BACKGROUND

Color of flour is an important sensory index and market index for evaluating the quality of wheat flour. As the most important natural pigments in wheat grains, yellow pigments are the primary cause for the yellowness of flour and products thereof. The yellow pigment content in grains has a correlation coefficient as high as 0.8 to 0.9 with the yellowness of flour and dough, and has correlation coefficients of 0.69 and 0.76 with the color of bread and noodles, respectively (Mares and Campbell, 2001; Adorn et al., 2003; Fratianni et al., 2005; Cong et al., 2010). Chinese-style flour products, such as white noodles, steamed breed, steamed buns, and dumplings, have relatively high requirements for the whiteness of flour, and white flour and products thereof are very popular.

Carotenoids are the main components of yellow pigments. Carotenoids, especially β-carotene, have important physiological health functions such as anti-oxidation, anti-cancer, provitamin A, preventing age-related macular degeneration, anti-aging, and improving immunity. Humans and animals cannot synthesize carotenoids by themselves and must uptake carotenoids from outside (Cazzonelli and Pogson, 2010). In recent years, with the enhancement of awareness of nutrition and health care, it has gradually become a new breeding goal to increase carotenoid content in wheat grains and cultivate wheat varieties that can provide bright-yellow flour and flour products.

Plant carotenoid biosynthesis involves a complex gene regulatory network (Cazzonelli and Pogson, 2010; Zhu et al., 2010). Lycopene cyclization is an important branch point in the carotenoid biosynthesis pathway. There are two types of lycopene cyclases in plants: LCYE and lycopene beta cyclase (LCYB). Howitt et al. (2009) cloned the Lcye gene in common wheat and used Sunco/Tasman DH1 population to co-segregate the gene with QTL of yellow pigment content on chromosome 3B, confirming that the Lcye gene is a key gene that affects yellow pigment content in grains. Dong (2011) cloned the full-length Lcye gene on chromosomes 3B and 3D in common wheat and developed a dominant marker YP3B-1 for the difference in B genome sequence. Crawford and Francki (2013) cloned the Lcye-3A gene and developed a functional marker-LCY3A-3 based on sequence differences. In summary, the current research on wheat Lcye gene is limited to QTL mapping, gene cloning, and molecular marker development, while the function and genetic regulation mechanism of the gene are still unclear, which severely restricts the progress of breeding work. Therefore, strengthening the study on gene function and genetic regulation mechanism of the Lcye gene will help to deeply understand the molecular mechanism of the formation of wheat yellow pigment content and lay the theoretical foundation for cultivating new wheat varieties with yellow pigment content meeting the market demand.

Targeting induced local lesions in genomes (TILLING) is a reverse genetics research method to obtain gene functions by quickly and efficiently detecting point mutations in target regions and identifying and analyzing the phenotype of the mutation, which effectively combines chemical mutagenesis method that induces high-frequency point mutations with PCR screening and high-throughput detection methods (Till et al., 2003a; Yan et al., 2014). Compared with molecular breeding technologies such as transgenesis and marker-assisted selection (MAS), the TILLING technology also has the advantages of stable and fast mutation breeding, only changing a single target trait, and no need to carry out time-consuming transgenesis, hybridization, and backcrossing processes, and thus is a highly efficient and targeted molecular breeding technology (Hou et al., 2008; Han et al., 2013). With the rapid development of sequencing technology and crop genomics, the TILLING technology will play an important role in the function analysis and genetic regulation of wheat genes and the genetic improvement of important agronomic and quality traits (Chen et al., 2010; Pan et al., 2011; Zhai et al., 2016).

SUMMARY

The present disclosure is intended to provide a mutant of an Lcye gene crucial in a wheat carotenoid synthesis pathway and use thereof.

In a first aspect, the present disclosure provides a protein.

The protein of the present disclosure may be any of the following: (A1) a protein obtained by substituting serine at position 253 of an LCYE-D1 protein with phenylalanine (S253F);

(A2) a protein derived from the protein defined in (A1), where, the protein is obtained by subjecting the protein defined in (A1) to substitution and/or deletion and/or addition of one or more amino acid residues and has the same ability as the protein defined in (A1);

(A3) a protein that has a homology of more than 99%, more than 95%, more than 90%, more than 85%, or more than 80% with the amino acid sequence defined in any one of (A1) and (A2) and has the same function as the amino acid sequence; and (A4) a fusion protein obtained by attaching a tag to N-terminus and/or C-terminus of the protein defined in any one of (A1) to (A3).

In the above protein, the tag refers to a polypeptide or protein that is fused with a target protein using DNA in vitro recombination technology and expressed, so as to facilitate the expression, detection, tracing, and/or purification of the target protein. The tag may be a Flag tag, a His tag, an MBP tag, an HA tag, a myc tag, a GST tag, an SUMO tag, etc.

Further, the protein shown in (A1) may be a protein composed of an amino acid sequence shown in SEQ ID NO. 1.

In a second aspect, the present disclosure provides a nucleic acid molecule encoding the protein described in the first aspect.

Further, the nucleic acid molecule may be a gene encoding the protein in the first aspect, and the gene may be a DNA molecule shown in any of the following:

(B1) a DNA molecule shown in SEQ ID NO. 2;

(B2) a DNA molecule that hybridizes with the DNA molecule defined in (B1) under stringent conditions and encodes the protein described in the first aspect; and (B3) a DNA molecule that has a homology of more than 99%, more than 95%, more than 90%, more than 85%, or more than 80% with the DNA sequence defined in (B1) or (B2) and encodes the protein described in the first aspect.

In the above gene, the stringent conditions may include the following: hybridizing at 50° C. in a mixed solution of 7% sodium dodecyl sulfate (SDS), 0.5 M $Na_3PO_4$, and 1 mM EDTA, and rinsing at 50° C. with 2×SSC, 0.1% SDS; hybridizing at 50° C. in a mixed solution of 7% SDS, 0.5 M $Na_3PO_4$, and 1 mM EDTA, and rinsing at 50° C. with 1×SSC, 0.1% SDS; hybridizing at 50° C. in a mixed solution of 7% SDS, 0.5 M $Na_3PO_4$, and 1 mM EDTA, and rinsing at 50° C. with 0.5×SSC, 0.1% SDS; hybridizing at 50° C. in a mixed solution of 7% SDS, 0.5 M $Na_3PO_4$, and 1 mM EDTA, and rinsing at 50° C. with 0.1×SSC, 0.1% SDS; hybridizing at 50° C. in a mixed solution of 7% SDS, 0.5 M $Na_3PO_4$, and 1 mM EDTA, and rinsing at 65° C. with 0.1×SSC, 0.1% SDS; and hybridizing at 65° C. in 6×SSC, 0.5% SDS, and rinsing with 2×SSC, 0.1% SDS and then with 1×SSC, 0.1% SDS.

In a third aspect, the present disclosure provides a recombinant vector, an expression cassette, a transgenic cell line, or a recombinant bacterial strain containing the nucleic acid molecule described in the second aspect.

In a fourth aspect, the present disclosure provides use of the protein described above, the nucleic acid molecule described above, or the recombinant vector, expression cassette, transgenic cell line, or recombinant bacterial strain described above in any of the following:

(C1) down-regulation of a total expression level of a wheat Lcye gene: or preparation of a product for down-regulating the total expression level of the wheat Lcye gene;

(C2) down-regulation of an expression level of a wheat Lcye-B1 and/or Lcye-D1 gene; or preparation of a product for down-regulating the expression level of the wheat Lcye-B1 and/or Lcye-D1 gene; and (C3) reduction of a yellow pigment content in wheat grains; or preparation of a product for reducing a yellow pigment content in wheat grains.

In a specific implementation of the present disclosure, the down-regulation of a total expression level of a wheat Lcye gene in (C1) and the down-regulation of an expression level of a wheat Lcye-B1 and/or Lcye-D1 gene in (C2) are specifically embodied at an RNA level. The down-regulation of a total expression level of a wheat Lcye gene refers to down-regulation of a total expression level of the Lcye gene in wheat grains; and the down-regulation of an expression level of a wheat Lcye-B1 and/or Lcye-D1 gene refers to down-regulation of the Lcye-B1 and/or Lcye-D1 gene in wheat grains.

In a fifth aspect, the present disclosure provides a method for reducing a yellow pigment content in wheat grains.

The method for reducing a yellow pigment content in wheat grains of the present disclosure may include the following steps: substituting only a codon in a recipient wheat genome that encodes serine at position 253 of an LCYE-D1 protein with a codon that encodes phenylalanine (preferably homozygous mutation).

Further, the substituting a codon in a recipient wheat genome that encodes serine at position 253 of an LCYE-D1 protein with a codon that encodes phenylalanine refers to substituting a gene in the recipient wheat genome that encodes an LCYE-D1 protein with a gene that encodes a protein consisting of an amino acid sequence shown in SEQ ID NO. 1.

Furthermore, the gene that encodes a protein consisting of an amino acid sequence shown in SEQ ID NO. 1 may be a DNA molecule shown in SEQ ID NO. 2.

In a sixth aspect, the present disclosure provides any use of the following: (D1) the use of the protein, the nucleic acid molecule, or the recombinant vector, expression cassette, transgenic cell line, or recombinant bacterial strain described above, or use of the method described above in the improvement of a color of wheat flour or flour products; and (D2) use of wheat varieties with a reduced grain yellow pigment content cultivated by the method described above in wheat breeding.

The present disclosure uses the TILLING technology to screen ethyl methane sulfonate (EMS)-mutagenized populations, designs specific primers according to a wheat Lcye sequence, detects mutation sites by non-denaturing polyacrylamide gel electrophoresis (PAGE) to obtain different mutant alleles of mutants, and conduct association analysis of different alleles with phenotypes to identify the influence of each mutation site on the function of LCYE. A total of 21 point mutations were detected in Lcye genes in 2.491 $M_2$ EMS-mutagenized populations, including 6 missense mutations, 2 synonymous mutations, and 13 intronic mutations. The Lcye gene has a mutation frequency of 1/266.1 kb in the populations. Predictive analysis of PARSENP software shows that two missense mutations M090815 (C2202T) and M091648 (G3284A) may seriously affect protein functions. MEME analysis results show that the mutation sites M090815 and M092230 (G2195A) are located in a conserved domain of Lcye gene. In the $F_2$ populations constructed by crossing the 6 missense mutants with the wild-type, the M090815 mutation site significantly reduces the yellow pigment content in grains, which confirms that this site has an important impact on the function of LCYE. qRT-PCR results show that the M090815 mutation site significantly reduces expression levels of the Lcye genes, where the expression levels of the Lcye-B1 and Lcye-D1 genes show the similar downward trends, while the Lcye-A1 gene shows the compensation effect from 14 to 28 days after anthesis. The present disclosure not only verifies the function of Lcye gene, but also provides a theoretical basis and a germplasm resource for improving the color of flour and products thereof.

DETAILED DESCRIPTION

Unless otherwise specified, the experimental methods used in the following examples are conventional methods.

The materials, reagents, etc. used in the following examples are all commercially available, unless otherwise specified.

Example 1

Study on the Function of a Lcye Gene Crucial in a Wheat Carotenoid Synthesis Pathway I. Materials and Methods Construction of EMS-Mutagenized Populations A method for constructing the EMS-mutagenized populations refers to the method of Slade et al. (2005). A batch of Jimai 20 (Ma et al., Effects of different water and nitrogen treatments on protein composition and processing quality of Jimai 20. Journal of Triticeae Crops, 2010, 30 (3): 477-481) and Jimai 22 (Liu et al., Changes of chlorophyll in flag leaves and enzyme activities in active oxygen scavenging system of high-yield Jimai 22, Shandong Agricultural Sciences, 2012, 44 (8): 31-34) seeds with stable homozygosity, uniform sizes, and full grains were first screened out: a chemical mutagen EMS with a concentration of 1.2% (Solarbio, E8150) was used for mutagenesis to produce a series of point mutations; treated seeds were grown in the greenhouse to obtain the $M_1$ mutant population; seeds of the $M_1$ were grown in field to obtain 2,491 Mw plants (Jimai 20: 1,251 plants; Jimai 22: 1,240 plants), and grains of each plant were harvested and stored, separately.

2. Screening an EMS Mutant Library with the TILLING Technology

EMS mutants were screened with reference to the method of Till et al. (2006). Specific steps were as follows:

Construction of the mutant DNA pool: A genomic DNA (gDNA) of each M: mutant was extracted with the CTAB method (Doyle and Doyle, 1987) and stored in a 96-well plate. A NanoDrop-2000 ultra-micro spectrophotometer (Thermo Scientific) was used to determine the concentration and quality of DNA. Every 8 samples were classified in a group, and DNAs thereof were mixed in equal amounts to construct the 8-fold DNA mixed pool, which was stored at 4° C. for later use.

Design of Lcye-specific primers: Based on the differences among homologous gene sequences of wheat Lcye, specific primers were designed for the A. B and D genomes. *Triticum dicoccoides*-nudigl nullisomic-tetrasomic materials (Ni et al., Cloning and identification of wheat transcription factor (TF) TaDREB6 gene. Journal of Triticeae Crops, 2008, 28 (3): 357-363) and PCR product sequencing methods were used to verify primer genome specificity; and the CODDLE (Codons Optimized to Discover Deleterious Lesions; proweb.org/coddle/) software was used to analyze whether the amplified region plays an important role in gene functions. Four pairs of Lcye-specific primers were obtained by screening (Table 1).

TABLE 1

Primer information for Lcye mutants screened by the TILLING technology

| Gene | Name | Sequence (5'-3') | Amplification length (bp) |
|---|---|---|---|
| Lcye-A1 | A3F- | F: CCACAGTAGCAAAAATTAGTCA (SEQ ID NO. 3) | 1450 |
| | A7R | R: TGCTACATTTCACAGTGGTGAA (SEQ ID NO. 4) | |
| Lcye-A1 | A8F- | F: GGTTGAAAGATATCCGTACAAC (SEQ ID NO. 5) | 978 |
| | A9R | R: TTTGGGTAACCGGAAAAAGGTT (SEQ ID NO. 6) | |
| Lcye-B1 | B4F- | F: CACCAACCCTGCACAAAGTGCC (SEQ ID NO. 7) | 578 |
| | B6R | R: GGAATATAAGACCACTCCTGAG (SEQ ID NO. 8) | |
| Lcye-D1 | D2F- | F: GCTGAGAAGGTACATTCTATCA (SEQ ID NO. 9) | 437 |
| | D5R | R: TTGAACTGGTGCACAAACAACA (SEQ ID NO. 10) | |

PCR amplification and heteroduplex generation: PCR amplification was conducted under the following conditions: template: DNA pools; reaction system: 15 μL in total: 50 ng of DNA, 7.5 μL of SuperMix (Transgen, AS111-01), 1 μL of each of upstream and downstream primers (10 μmol·L$^{-1}$), and the balance of ddH$_2$O; reaction procedure: first 95° C. for 5 min, then 95° C. for 30 s; starting from 66° C., annealing at a temperature reduced by 0.3° C. for each cycle, annealing time: 45 s, 72° C. for 1.5 min, a total of 35 cycles; extension at 72° C. for 10 min, then at 99° C. for 10 min, and 85° C. for 1 min; starting from 85° C., annealing at a temperature reduced by 0.5° C. for each cycle, annealing time: 30 s, a total of 99 cycles; incubation at 16° C. for later use. If there is a mutation site in the target fragment sequence of DNA mixed pool sample, the amplification product can undergo repeated denaturation and renaturation to form a heteroduplex (namely, with mismatched bases) of wild-type and mutant amplified fragments.

CEL I digestion: CEL I (endonuclease) that specifically recognizes and cleaves mismatched bases was used to cleave heteroduplex nucleic acid molecules. The extraction method of CEL I refers to the method of Till et al. (2006). After the enzyme activity of CEL I was confirmed, the effects of CEL I concentration, digestion time, digestion temperature, and digestion buffer concentration on the digestion effect were analyzed to optimize the digestion system, according to the method of Panna et al. (2012). The optimal digestion reaction system was determined as follows: 20 μL in total: 2 μL of 10× digestion buffer, 1 μL of CEL I, 15 μL of heteroduplex DNA, and the balance of ddH$_2$O. The digestion reaction was conducted at 45° C. for 20 min, and then 5 μL of EDTA (0.25 M, Sangon Biotech Co., Ltd., ET0895) was added to terminate the digestion reaction.

Non-denaturing PAGE detection: The non-denaturing PAGE detection technology was used to screen out positive DNA pools with mutation sites. Each DNA in the positive DNA pool was mixed with wild-type DNA one by one, and the above step was repeated to screen out positive mutant individuals.

Cloning and sequencing of mutants: Cloning and sequencing were conducted on PCR products of mutants to identify the type and location of mutations.

Prediction of the Effects of Mutation Sites on Protein Functions

Project aligned related sequences and evaluate SNP (PARSESNP; proweb.org/parsesnp/) software was used to analyze the mutation type of the DNA sequence in the mutant plant and predict whether the mutation site will affect the function of LCYE. When the PSSM value is greater than 10 and the sorting intolerant from tolerant (SIFT) value is less than 0.05, amino acid alterations are considered to have a significant impact on protein functions (Ng and Henikoff, 2003; Taylor and Greene, 2003).

Functional Analysis of Mutation Sites

In order to reduce the influence of other mutation backgrounds, homozygous $M_3$ plants with missense mutation sites in the Lcye gene were crossbred with wild-type plants to construct $F_2$ populations (Grains of six $M_2$ plants with missense mutation sites in the Lcye gene were harvested and planted in the field, the genotype of the $M_3$ plants was identified by cloning and sequencing, and three homozygous mutants were selected and crossbred with corresponding wild-type plants to construct $F_2$ populations. $F_0$ grains were harvested from three hybrid ears, $F_0$ plants were selfed to obtain $F_1$ grains, and $F_1$ grains were sown to obtain $F_2$ populations), which were used to analyze the effects of mutation sites on gene expression levels and protein function. The $F_2$ populations were planted in Jinan, Shandong from 2017 to 2018, with the row length of 3 in, the row spacing of 25 cm, 30 plants per row, and 15 rows for each $F_2$ population. The field management adopted to the conventional method.

The method of cloning and sequencing was used to identify the Lcye genotype (homozygous mutant, heterozygous mutant, and wild type) of each plant in the $F_2$ populations. For each genotype, 10 biological replicates with consistent growth and development processes were selected. The anthesis was recorded, and grains were collected at 7, 14, 21, and 28 days after anthesis and immediately stored in liquid nitrogen at −80° C., which would be used to analyze the expression level of the Lcye gene. Mature grains were harvested from each single plant, respectively, and stored at −20° C., which would be used to determine the yellow pigment content.

The qRT-PCR technology was used to determine the expression levels of Lcye gene and homologous genes thereof at different developmental stages of grains of homozygous mutant, heterozygous mutant, and wild-type plants in the $F_2$ populations (7, 14, 21, and 28 days after anthesis), and the influence of mutation sites on the expression level of Lcye gene was analyzed. Specific steps: RNAprep Pure kit (TIANGEN Biotech, DP441) was used to extract total RNA from grains, with three biological replicates for each of homozygous mutant, heterozygous mutant, and wild-type plants; PrimeScript™ RT Reagent kit (Takara Bio Inc., RR047A) was used to reverse-transcribe the RNA into cDNA, which was stored at −20° C. for later use; based on the conservation and difference among cDNA sequences of wheat Lcye homologous genes, conserved primers and A, B, D genome-specific primers were designed for Lcye genes (Table 2), and the melting curve analysis and the cloning and sequencing of qRT-PCR products were conducted to verify the conservation and specificity of the primers; the common wheat β-actin gene (AB181991) was adopted as the internal reference gene; the qRT-PCR technology was used to detect the expression levels of Lcye gene at different developmental stages of grains of homozygous mutant, heterozygous mutant, and wild-type plants in the $F_2$ populations, with three technical replicates for each sample, where the relative gene expression level was expressed by mean±standard error (SE). Reaction system: 20 μL in total: 10 μL of LightCycler FastStart DNA Master SYBR Green (Roche Applied Sciences. No. 03003230001), 0.5 μM upstream and downstream primers, 50 ng of cDNA, and the balance of ddH$_2$O. Reaction program: 95° C. for 10 min; 95° C. for 15 s, 60° C. for 20 s, and 72° C. for 20 s, a total of 40 cycles. The formula $2^{-\Delta\Delta CT}$ was used to calculate the relative expression level of the target gene (Livak and Schmittgen, 2001). The transcriptional level of the s-actin gene in the same sample was used to correct the relative expression level of the target gene. The relative expression level of the target gene in grains of wild-type plants at 28 days after anthesis was set as 1, and then relative expression levels of the target gene in grains of plants with different genotypes at different developmental stages were calculated.

Table 2 qRT-PCR primer information of Lcye gene

| Gene | Name | Sequence (5'-3') |
|---|---|---|
| Lcye-all | Lcye-all-F2 | TGACCACYGAATATCCAGTTGC (SEQ ID NO. 11) |
| | Lcye-all-R6 | AGTTTTCTTTGAGGAAACATGC (SEQ ID NO. 12) |
| Lcye-A1 | Lcye-A1-F7 | GTTGCTGAGAAGATGCAACGAT (SEQ ID NO. 13) |
| | Lcye-A1-R7 | CAAAGTATCTTGCGGTCCCTTT (SEQ ID NO. 14) |
| Lcye-B1 | Lcye-B1-F3 | ATCTCCAGATGGACATCGAGTG (SEQ ID NO. 15) |
| | Lcye-B1-R3 | TCCAACCTCATACTCTAGAAGT (SEQ ID NO. 16) |
| Lcye-D1 | Lcye-D1-F3 | TTGGCCCTGATCTTCCATTC (SEQ ID NO. 17) |
| | Lcye-D1-R1 | ATATACTACTCGATGTCCATCA (SEQ ID NO. 18) |
| β-actin | Actin-F | CTGATCGCATGAGCAAAGAG (SEQ ID NO. 19) |
| | Actin-R | CCACCGATCCAGACACTGTA (SEQ ID NO. 20) |

The yellow pigment content in grains was determined for homozygous mutant, heterozygous mutant, and wild-type plants in the $F_2$ populations, and the influence of mutation sites on the function of LCYE was analyzed. The method for determining the yellow pigment content in grains refers to AACC methods 14 to 50, with minor changes. Briefly, 1 g of whole wheat flour was weighed, and extraction under shaking was conducted with water-saturated n-butanol (at a volume ratio of 5:1) for 1 h; and the resulting solution was centrifuged at 5,000 rpm for 10 min. The absorbance microplate reader (moleculardevices.com) was used to determine the absorbance of a supernatant at 436.5 nm, and then the yellow pigment content was calculated. Three technical replicates were adopted for each sample, and the yellow pigment content was expressed by mean f SE.

5. Prediction of Functional Domains of LCYE

National center for biotechnology information (NCBI; ncbi.nlm.nih.gov/) database was used to obtain cDNA sequences of Lcye genes of 27 species (Table 3), and MEME Suite 5.1.0 (meme-suite.org/) was used to predict the functional domains of LCYE, and the distribution of mutation sites in the domains was analyzed.

TABLE 3 cDNA sequence information of Lcye gene of 27 species

| Species name | Genbank accession number |
|---|---|
| Arabidopsis thaliana | NM_125085 |
| Brachypodiumdistachyon | XM_003569209 |
| Brassica rapa | XM_009133907 |
| Capsella rubella | XM_006280236 |
| Chlamydomonas reinhardtii | XM_001696477 |
| Citrus sinensis | AY533827 |
| Cucumis sativus | XM_004157912 |
| Fragaria vesca | XM_004287534 |
| Glycine max | XM_003533727 |
| Hordeum vulgare | AK371513 |
| Linumusitatissimum | KC565894 |
| Malus domestica | XM_008389970 |
| Medicago truncatula | XM_003595195 |
| Oryza sativa | NM_001049945 |
| Physcomitrella patens | XM_001753846 |
| Prunus persica | XM_007203578 |

TABLE 3-continued cDNA sequence information of Lcye gene of 27 species

| Species name | Genbank accession number |
|---|---|
| Ricinus communis | XM_002514090 |
| Setaria italica | XM_004969360 |
| Solanum lycopersicum | EU533951 |
| Solanum tuberosum | XM_006353482 |
| Sorghum bicolor | XM_002455793 |
| Theobroma cacao | XM_007012707 |
| Triticum aestivum | EU649785 |
| Triticum turgidum | GAKM01004311 |
| Triticum urartu | GAKL01018490 |
| Vitis vinifera | JQ319637 |
| Zea mays | EU924262 |

6. Statistical Analysis

The Student's t test was used to analyze differences in the Lcye gene expression and yellow pigment content in grains of homozygous mutant, heterozygous mutant, and wild-type plants in the $F_2$ populations.

II. Results

Screening of EMS-Induced Mutant Library

Figure 1:
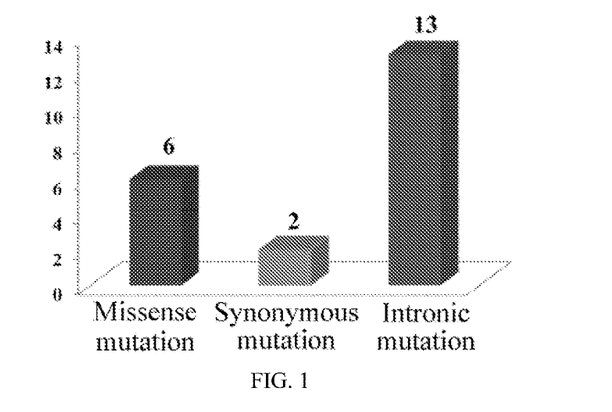
FIG. 1 shows the mutation types of Lcye.

A total of 21 Lcye gene mutants were detected with the TILLING technology among 2,491 $M_2$ EMS-mutagenized populations (Table 4). Cloning and sequencing and sequence analysis showed that the mutation frequency of nucleotides from C to T was 57.14%, the mutation frequency from G to A was 38.10%, and one specific mutation site from T to C was also detected. According to the mutation positions, eight were located in the exon region and 13 were located in the intron region. Point mutations in the exon region were further divided into six missense mutations and two synonymous mutations (FIG. 1).

TABLE 4

Information of Lcye mutants screened out by the TILLING technology

| Gene | Mutant No. | Exon/intron | Nucleotide alteration | Codon alteration | Amino acid alteration | Genotype |
|---|---|---|---|---|---|---|
| Lcye-A1 | M091034 | Intron | C1184T | | | Hom |
| | M091686 | Intron | C1243T | | | Hom |
| | M091772 | Intron | C1418T | | | Hom |
| | M092043 | Intron | C1478T | | | Hom |
| | M092852 | Intron | C3222T | | | Hom |
| | M090431 | Intron | C858T | | | Het |
| | M090631 | Intron | T1461C | | | Het |
| | M090897 | Intron | G1068A | | | Hom |
| | M091996 | Intron | G1575A | | | Hom |
| | M090147 | Intron | G3073A | | | Hom |
| | M091648 | Exon | G3284A | GGA→GAA | G392E | Hom |
| | M090201 | Exon | G3306A | TTA→TTG | L399= | Hom |
| Lcye-B1 | M091626 | Intron | G2406A | | | Hom |
| Lcye-D1 | M092404 | Intron | C2014T | | | Het |
| | M091884 | Intron | C2017T | | | Het |
| | M090945 | Exon | C2086T | TAC→TAT | Y214= | Hom |
| | M092089 | Exon | C2087T | CTC→TTC | L215F | Hom |
| | M091328 | Exon | C2121T | CCT→CTT | P226L | Het |
| | M090815 | Exon | C2202T | TCT→TTT | S253F | Het |
| | M092230 | Exon | G2195A | GCA→ACA | A251T | Hom |
| | M091075 | Exon | G2262A | GGT→GAT | G273D | Hom |

Notes:
Hom: homozygous mutant; Het: heterozygous mutant. Each mutant in the table has only one corresponding mutation in the Lcye gene, that is, one mutant does not have multiple mutations in the Lcye gene.

In the present disclosure, conventional non-denaturing PAGE was used to separate the CEL I digestion product, and mismatches within 0.15 kb at both ends of the fragment would exceed the detection range, so the accumulative length of effective target fragments for Lcye gene screened was 2.24 kb (Table 1). The screening population included 2.491 $M_2$ plants, and it was inferred that the Lcye gene had the mutation density of 1/266.1 kb in the EMS-mutagenized population.

Prediction of the effects of mutation sites on protein functions: Analysis results of the PARSESNP software showed that the PSSM values of missense mutants M090815 (C2202T) and M091648 (G3284A) were 26.9 and 27.7, respectively, and the SIFT values were 0. It was inferred that these mutation sites may have a significant impact on protein functions (Table 4).

TABLE 4

Prediction of the impact of mutation sites on protein function

| Gene | Mutant No. | Nucleotide alteration | Amino acid alteration | PSSM value | SIFT value |
|---|---|---|---|---|---|
| Lcye-D1 | M090815 | C2202T | S253F | 26.9 | 0 |
| Lcye -A1 | M091648 | G3284A | G392E | 27.7 | 0 |

Notes:
The genomic sequence of the mutated Lcye-D1 gene in the missense mutant M090815 (C2202T) is shown in SEQ ID NO. 2, which encodes the mutated LCYE-D1 protein shown in SEQ ID NO. 1.

Analysis of the Lcye Gene Expression and Yellow Pigment Content in Mutants

Homozygous missense mutants were crossbred with wild-type plants to construct six $F_2$ populations, and the effects of mutation sites on the Lcye gene expression level and grain yellow pigment content were analyzed. Results showed that, in six $F_2$ populations, only the M090815 (C2202T) mutation site significantly reduced the Lcye gene expression level and yellow pigment content (FIG. 2 and FIG. 3), indicating that this mutation site has an important impact on the function of LCYE protein.

Figure 2:
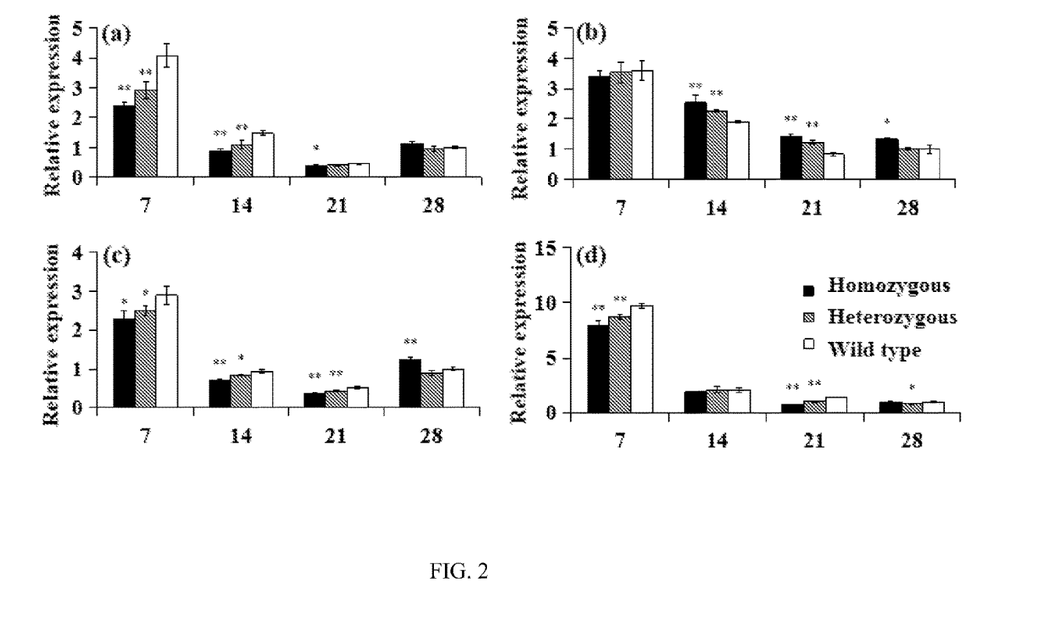
FIG. 2 shows the relative expression levels of Lcye and its homologous genes in the grains of different genotypes in the $F_2$ populations of the mutant M090815, where, * and ** represent significance levels of 0.05 and 0.01, respectively, and (a) Lcye-all, (b) Lcye-A1, (c) Lcye-B1, and (d) Lcye-D1.
Figure 3:
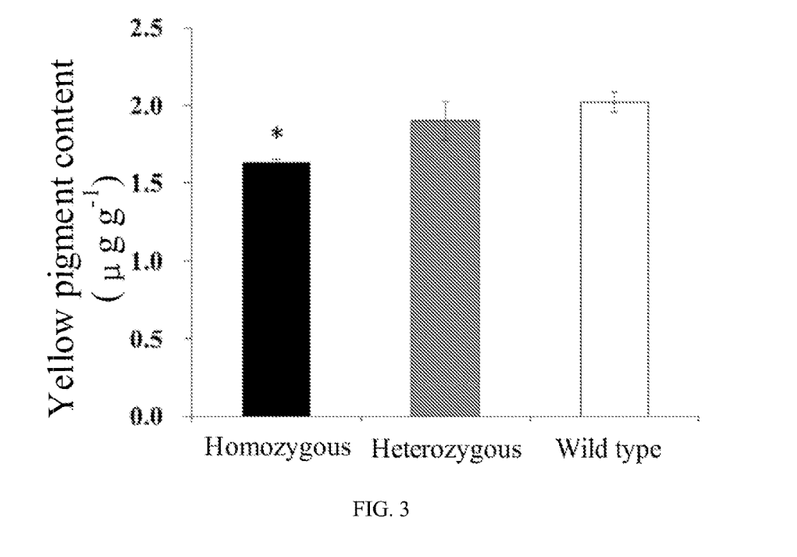
FIG. 3 shows the yellow pigment contents in grains of three genotypes in the $F_2$ populations of the mutant M090815, where, * represents the significance level of 0.05.

The expression levels of Lcye and homologous genes thereof were shown in FIG. 2. From 7 to 21 days after anthesis, the total expression level of the Lcye gene in grains of homozygous mutants decreased to 9% to 83% of that in wild type plants, and the total expression level of the Lcye gene in grains of heterozygous mutants decreased to 71% to 91% of that in wild type plants. There was no significant difference in the expression among genotypes at 28 days after anthesis. The expression levels of Lcye-B1 and Lcye-D1 genes showed a similar trend. At each stage after anthesis, the expression level in homozygous mutant plants decreased to 56% to 92% of that in wild type plants, and the expression level in heterozygous mutant plants decreased to 75% to 90% of that in wild type plants. However, the expression level in Lcye-B1 homozygous mutants was significantly higher than that in the wild type plants at 28 days after anthesis. Lcye-A1 showed no significant difference among the expression levels of various genotypes at 7 days after anthesis, and showed the compensation effect from 14 to 28 days after anthesis. The expression level of Lcye-A1 in homozygous mutants was 33% to 70% higher than that in wild type plants, and the expression level in heterozygous mutants was 1% to 48% higher than that in wild type plants. Correspondingly, in the $F_2$ population constructed by the mutant M090815, the yellow pigment content in mature grains of homozygous mutants was significantly lower than that in heterozygous mutants and wild type plants (FIG. 3, 1.63 vs 1.90, and 2.02).

Figure 4:
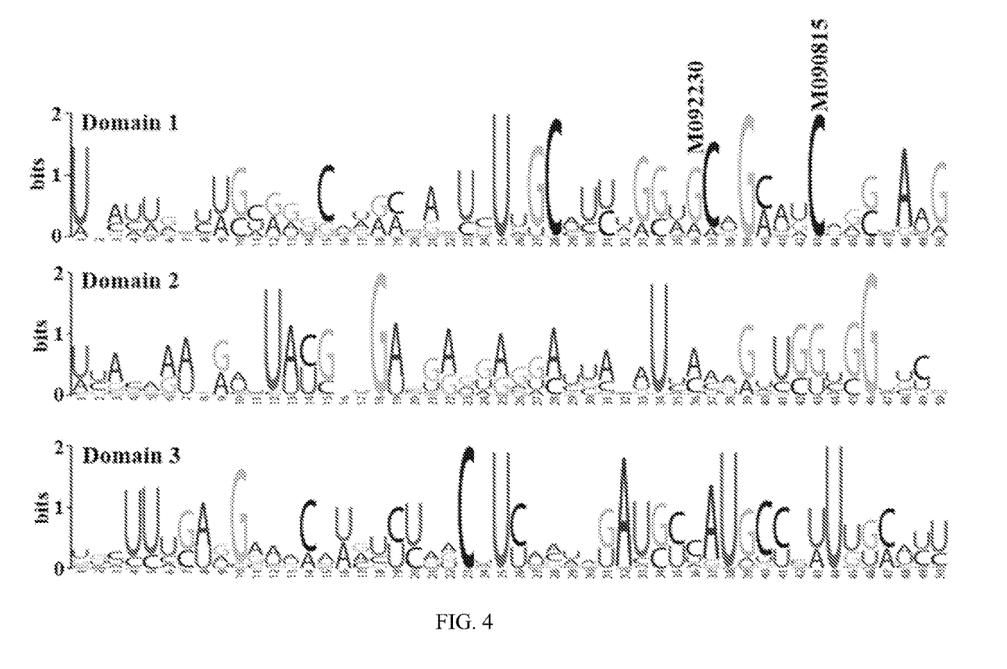
FIG. 4 shows the prediction of the functional domains of Lcye.

Prediction of functional domains of LCYE: Based on the known cDNA sequences of Lcye gene in 27 species including *Arabidopsis thaliana, Orza sativa*, and *Hordeum vulgare*, MEME Suite 5.1.0 was used to predict the functional domains of LCYE, and a total of three domains were detected (FIG. 4). Among six missense mutations, the mutation sites of M090815 (C2202T) and M092230 (G2195A) were located in domain 1: the mutation site of M090815 was conserved in the 27 species; and the M092230 mutation site involved the variation of G, A and U bases.

III. Discussion 1. LCYE Regulates the Carotenoid Synthesis in Wheat Grains

The carotenoid content in wheat grains affects the nutritional quality and apparent color of flour products. The carotenoid content and composition dynamically change during the development process, exhibiting a complex network regulation mechanism (Howitt et al., 2009). Lycopene cyclization is an important branch point in the carotenoid synthesis pathway, and different products are generated through two pathways: carotenoids such as zeaxanthin, antheraxanthin, and violaxanthin are generated through the β-β pathway; and lutein is eventually generated through the other β-ε pathway. The β-β pathway carotenoid products have a relatively-high expression level at the early development stage of common wheat grains, and with the growth and development of grains, the expression level and proportion of the β-β pathway carotenoid products gradually decrease. There were almost no zeaxanthin, antheraxanthin, and violaxanthin in mature grains. On the contrary, the accumulation of lutein is relatively stable at all development stages of grains, and lutein is the main component of carotenoids in mature grains (Howitt et al., 2009).

By adjusting the relative activity and content of LCYB and LCYE, proportions of α-carotene and β-carotene converted from substrates can be determined. In a tomato Delta mutant (Hornero-Mendez et al., 2000), the 8-carotene content in fruits greatly increases due to the increase of Lcye transcriptional level; while in the tomato Beta mutant, the large amount of β-carotene accumulates in fruits due to the overexpression of Lcyb. The comparison between the two tomato mutants further confirms that the accumulation of carotenoids in tomato fruits is mainly due to the differential expression of related genes at the transcriptional level (Ronen et al., 2000).

The TILLING technology effectively combine high-frequency point mutation with modern analysis technique, which can be used to not only obtain a series of point mutation alleles, but also screen the target gene mutants with only a small mutant population (Till et al., 2003b). Richaud et al. (2018) used the TILLING technology to screen durum wheat Lcye mutants. The W437* (Lcye-A1) mutation site significantly increases the β-carotene and carotenoid contents in leaves of the mutants, but shows no significant influence on the carotenoid content in grains. In the present disclosure, the TILLING technology is used to screen a common wheat EMS-induced mutant library to obtain a series of allelic variation of Lcye genes, and their effects on the gene expression and grain yellow pigment content is studied, which lays theoretical foundation and provides important germplasm resources for the research on gene functions and the improvement of flour products color.

2. Screening of Lcye Mutants

The TILLING technology effectively combines high-frequency point mutations of chemical mutagenesis with fast and simple mutant detection technologies, which can quickly and effectively detect point mutations of the target genes from mutant populations, and has gradually become an important tool in research of plant functional genomics, crop genetics and breeding, and genetic diversity assessment of natural resources (Gilchris and Haughn, 2005; Till et al., 2018). At present, the technology has been widely used in more than 20 crops such as *Oryza sativa* (Till et al., 2007). *Zea mays* (Till et al., 2004), *Triticum* (Acevedo-Garcia et al., 2017; Kim et al., 2018), *Hordeum vulgare* (Gottwald et al., 2009), *Glycine max* (Hoshino et al., 2010), and *Sorghum bicolor* (Nida et al., 2016).

The gene mutation frequency in wheat is much higher than that in *Arabidopsis thaliana*, rice and corn. The TILLING technology has a huge application potential and a bright prospect in wheat and other Triticeae crops. For polyploid species with complex genomes, multiple gene copies result in a bottleneck restricting the efficient application of TILLING technology. It is very important to design specific primers, which will affect the detection efficiency. There is a high sequence similarity (89.1% to 97.0%) among homologous genes of wheat Lcye genes A, B, and D, so it is very difficult to design specific markers. In combination with the possible range of EMS-induced harmful mutations in plants given by the CODDLE program, four pairs of primers are finally screened out for Lcye mutant detection (Table 1). A total of 21 Lcye mutation sites are screened out, the mutation frequency from G/C to A/T is 95.24%, and the mutation frequency from T to C is 4.76%.

There are many methods for detecting digestion products, such as high-performance liquid chromatography (HPLC), PAGE, agarose gel electrophoresis and two-color infrared fluorescence detection (Colbert et al., 2001; Dong et al., 2009; Uauy et al., 2009; Colasuonno et al., 2016). The present disclosure adopts the non-denaturing PAGE detection technology, and adopts neither fluorescently-labeled primers nor expensive denaturing gel electrophoresis imaging systems, which effectively simplifies the experimental procedure, reduces the experimental cost, and expands the application scope and efficiency of TILLING to a certain extent.

Important Regulatory Sites Affecting LCYE Functions

Based on the cDNA sequences of Lcye in 27 species such as *Arabidopsis thaliana, Oryza sativa*, and *Hordeum vulgare*. MEME is used to predict the functional domains of LCYE, and results show that the mutation sites of M090815 (C2202T) and M092230 (G2195A) are just located in domain 1 (FIG. 4). The M092230 (G2195A) mutation site involves three base variations of G. A, and U in the evolution of natural species. Therefore, it is inferred that the G to A nucleotide mutations have no effect on the function of LCYE. The M090815 (C2202T) mutation site is much conserved in 27 species, and it is inferred that this site has an important impact on the function of LCYE. In the $F_2$ population constructed by M090815, compared with the wild-type plants, the yellow pigment content in grains of homozygous mutant plants is significantly decreased (FIG. 3), indicating that the M090815 (C2202T) mutation site has an important impact on the function of LCYE.

Prediction results by PARSESNP software show that the M090815 (C2202T) and M091648 (G3284A) mutation sites may have a significant effect on protein functions (Table 4). It further confirms the importance of the M090815 (C2202T) mutation site to the function of LCYE protein. However, in the $F_2$ population constructed by M091648, the yellow pigment content between homozygous mutant plants and wild-type plants is not significantly different. This inconsistency may be due to the fact that the PARSESN software predicts the severity of the impact of mutation sites on protein function based on the sequence homology and the physical properties of amino acids, because some sites may not participate in protein function regulation (Ng and Henikoff, 2003; Taylor and Greene, 2003).

The expression levels of Lcye and homologous genes in the $F_2$ population constructed by M090815 shows that the total expression level of Lcye gene in grains of homozygous mutant plants is significantly lower than that of the wild-type plants (FIG. 2). At each development stage of grains, except that the expression level of the Lcye-B1 homozygous mutant is higher than that of the wild type plant at 28 days after anthesis, the expression levels of Lcye-B1 and Lcye-D1 genes show a downward trend. However, the expression level of Lcye-A1 shows no significant difference among various genotypes at 7 days after anthesis, and shows the compensation effect from 14 to 28 days after anthesis. It is speculated that the expressions of Lcye-B1 and Lcye-D1 genes are coordinately regulated, while the regulation mechanism of Lcye-A1 expression may be different. Given that the above results are obtained merely through one $F_2$ population, this speculation still needs to be verified subsequently. Sequence analysis shows that the Lcye-B1 gene has high sequence similarity with the Lcye-D1 gene reaching to 97.0%, while the Lcye-A1 gene has sequence similarities of 89.1% and 89.2% with the Lcye-B1 and Lcye-D1 genes, which provides indirect support for the above speculation.

Molecular Breeding

The lack of germplasm resources has become a bottleneck in the improvement of the color of wheat flour and products thereof, which seriously affects the genetic improvement of the flour color character in China. EMS mutagenesis can create a large number of allelic variations, which are inherited stably in offspring. Since no transgenic operations are involved, excellent mutants obtained can be directly used in breeding practices (Hou et al., 2008; Slade et al., 2012). In China, flour products are mainly cooked in manners of steaming and stewing, and delicate and white flour is favored by consumers. In this study, the M090815 mutant screened out by the TILLING technology, which significantly reduces the yellow pigment content in grains, can be used as an important germplasm resource for the genetic improvement of flour color. In addition, Jimai 20 is a high-yield and high-quality strong gluten wheat that can be used for making both bread and noodles; and Jimai 22 is a super-high-yield, stable-yield, wide-adapted, multi-resistant wheat variety, both of which are excellent varieties with prominent comprehensive traits that are popularized in a large area. Excellent mutants generated by using these two varieties are more suitable for being use as hybrid parents, with a view to quickly cultivating new high-yield and high-quality wheat varieties.

What is claimed is:

1. A Lycopene Epsilon Cyclase (LCYE) protein, comprising the amino acid sequence shown in SEQ ID NO. 1.

2. A gene, a wheat plant comprising said gene, a recombinant vector, an expression cassette, a transgenic cell line, or a recombinant bacterial strain encoding the protein according to claim 1.

3. A method for reducing a yellow pigment content in wheat grains, comprising the following step: substituting a codon in a recipient wheat genome that encodes serine at position 253 of a Lycopene Epsilon Cyclase (LCYE) protein with a codon that encodes phenylalanine, wherein the resulting LCYE protein is encoded by the amino acid sequence shown in SEQ ID NO. 1.

* * * * *

SEQUENCE LISTING

<160> NUMBER OF SEQ ID NOS: 20

<210> SEQ ID NO 1
<211> LENGTH: 536
<212> TYPE: PRT
<213> ORGANISM: Artificial Sequence
<220> FEATURE:
<223> OTHER INFORMATION: S253F

<400> SEQUENCE: 1

Met Glu Ser Thr Gly Ala Ala Ile Ser Ala Pro Phe Gly Cys Arg Ala
1               5                   10                  15

```
Leu Arg Trp Ala Gly Gln Arg Pro Leu Arg Pro Ala Asp Gly Arg Arg
            20                  25                  30

Arg Arg Val Gly Pro Gly Pro Gly Pro Glu Lys Trp Arg Ser Leu Lys
        35                  40                  45

Ala Ser Cys Val Ala Thr Glu Lys Pro Asp Glu Lys Ala Ala Pro Gly
50                  55                  60

Leu Gly Val Glu Phe Ala Asp Glu Glu Asp Tyr Val Lys Gly Gly Gly
65                  70                  75                  80

Gly Glu Leu Leu Tyr Val Gln Met Gln Ala Thr Lys Ala Met Glu Ser
                85                  90                  95

Gln Ser Lys Ile Ala Ser Lys Leu Leu Pro Ile Ala Asp Glu Thr Ser
                100                 105                 110

Val Leu Asp Leu Val Ile Ile Gly Cys Gly Pro Ala Gly Leu Ser Leu
            115                 120                 125

Ala Ala Glu Ser Ala Lys Lys Gly Leu Thr Val Gly Leu Ile Gly Pro
        130                 135                 140

Asp Leu Pro Phe Thr Asn Asn Tyr Gly Val Trp Glu Asp Glu Phe Lys
145                 150                 155                 160

Asp Leu Gly Leu Glu Ser Cys Ile Glu His Val Trp Lys Asp Thr Val
                165                 170                 175

Val Tyr Leu Asp Arg Asn Lys Pro Ile Met Ile Gly Arg Ala Tyr Gly
            180                 185                 190

Arg Val Asp Arg Asp Leu Leu His Glu Glu Leu Leu Arg Arg Cys Asn
        195                 200                 205

Glu Ala Gly Val Thr Tyr Leu Asn Ser Lys Val Glu Gln Ile Lys Glu
    210                 215                 220

Ser Pro Asp Gly His Arg Val Val Tyr Cys Gly Arg Gly His Lys Ile
225                 230                 235                 240

Leu Cys Arg Leu Ala Ile Val Ala Ser Gly Ala Ala Phe Gly Lys Leu
                245                 250                 255

Leu Glu Tyr Glu Val Gly Gly Pro Arg Val Cys Val Gln Thr Ala Tyr
            260                 265                 270

Gly Val Glu Val Glu Val Glu Arg Tyr Pro Tyr Asp Pro Ser Leu Met
        275                 280                 285

Val Phe Met Asp Tyr Arg Asp Cys Phe Lys Glu Lys Phe Thr His Pro
    290                 295                 300

Glu Glu Ala Asn Pro Thr Phe Leu Tyr Ala Met Ala Met Ser Ser Thr
305                 310                 315                 320

Arg Val Phe Phe Glu Glu Thr Cys Leu Ala Ser Lys Asp Ala Met Pro
                325                 330                 335

Phe Asp Leu Leu Lys Lys Arg Leu Met Ser Arg Leu Asp Ala Met Gly
            340                 345                 350

Val Arg Ile Ile Lys Val Tyr Glu Glu Glu Trp Ser Tyr Ile Pro Val
        355                 360                 365

Gly Gly Ser Leu Pro Asn Thr Asp Gln Lys Asn Leu Ala Phe Gly Ala
    370                 375                 380

Ala Ala Ser Met Val His Pro Ala Thr Gly Tyr Ser Val Val Arg Ser
385                 390                 395                 400

Leu Ser Glu Ala Pro Arg Tyr Ala Ser Val Ile Ser Asp Ile Leu Arg
                405                 410                 415

Asn Arg Val Tyr Ser Gly Gln Tyr Leu Pro Gly Ser Ser Glu Met Ser
            420                 425                 430

Ser Pro Ser Met Leu Ala Trp Gly Thr Leu Trp Pro Gln Glu Arg Lys
```

```
                    435                 440                 445
Arg Gln Arg Ser Phe Phe Leu Phe Gly Leu Ala Leu Ile Ile Gln Leu
    450                 455                 460

Asp Asn Glu Gly Ile Gln Thr Phe Phe Glu Ser Phe Phe Arg Leu Pro
465                 470                 475                 480

Lys Trp Met Trp Arg Gly Phe Leu Gly Ser Thr Leu Ser Ser Ala Asp
                485                 490                 495

Leu Met Leu Phe Ala Leu Tyr Met Phe Ala Ile Ala Pro Asn Thr Leu
            500                 505                 510

Arg Met Asn Leu Val Arg His Leu Leu Ser Asp Pro Thr Gly Ser Ala
        515                 520                 525

Met Ile Arg Thr Tyr Leu Thr Leu
    530                 535

<210> SEQ ID NO 2
<211> LENGTH: 3739
<212> TYPE: DNA
<213> ORGANISM: Artificial Sequence
<220> FEATURE:
<223> OTHER INFORMATION: gene encoding the protein

<400> SEQUENCE: 2
atggagtcca ccggcgccgc catctcggcg ccgttcggct gccgcgcgtt gcgctgggcc     60
gggcagcggc ctctccggcc ggccgatggc aggagaaggc gggtgggtcc gggccccggg    120
ccggagaagt ggaggagctt gaaggcgagc tgcgtggcca ggagaagcc cgacgagaag    180 gcggcgccgg gctaggggt ggagtttgcc gacgaggagg actacgtcaa gggcggcggc    240
ggtgagctgc tctacgtgca atgcaggcc accaaggcca tggaaagcca gtccaagatc    300
gcctccaagg ttctctctct atccttttat gtactgctac cgctagtctg ctactgctag    360
tggtatcttg ttctttgttt tattccctta tttaattgct gatttctatg catgttttgt    420
tgatcttgaa atactactc tagtacttaa gtgattcttt ccccaatta gcgttgtgtg    480 aacttccagc gttatggcga ataaaattaa atccctaac attagtctgt tctttcttg    540 cgatgtacag tagtaacatt agactgtttg aaagatgaag gattcccata acaccacag    600 tagcaaaaat taatctgggt actattgcat actatactac tccctccgta tcaaaatata    660
agaccagaaa atacatagga gctcttgggt gctccacacc ctatatgaat attaaacgta    720 aaaaatacc aaaaaattaa aaatctgaa atttggggat attaaacctg gttcttaat    780 ctactcccgt gtgaaatttt gtgaaaaaat accagcacac gtatccgtgg cgaaggaaat    840
attgtccgaa caaaaatcca tccaaacagt ttttctata cataggaatt ttttgtcttt    900
tttgccacga atatgtttcc tggtattttt ttcacgaaat tttacacggg agtagatcgg    960
gaacccaggt ttgatatccc aaaatcttag ttttttttca aatttctcgg tattttttta   1020
aatttaatgt tcgtgtaggg gtgtggagca accgggtgct acaaatccgc ttccatccaa   1080 agggggtctta tatttggata tagagggagt agaacgcaag tggcattcaa atgcacgtca   1140
tgctagtact accatggcgt tgctcatttt tgacaaatca gggatagtct tgggtcgccc   1200
atgcttgtca ttcctgcctt cctggcagga gcagagtaca caatgtattt ggtcttgcgt   1260
taattaattg ctccttaggg acatgtcttt ggtcgtgcct ttgacttgct ttctttggaa   1320 acgcccttc actaagtata tcattcaata attcctacat agcaagacgc ggatcttagt   1380 gggtacgaa cgtcattgtg tacatgtttc aatcctctt ttactgatac tctgtacagt   1440
tctttttctt caaggttaat taattaagtt tcgaagttca tcgtcatttt gttaacaatt   1500
```

```
ttttgtctgg tagcatcctt caagtagttg attatgtctt ctgaatctttt ctttgcagct    1560 gttgcctata gctgatgaaa cttcagtgct tgatttggtt atcattggct gtggtccagc    1620
cggcctatct ctggctgcag aatcagcaaa gaaaggactc actgttggtc tcattggccc    1680
tgatcttcca ttcacaaaca attacggtgt atggggagga gaattcaaag gtagccatta    1740
gtcgcagctg tgaaatgcag caccatgctt ggataacatc tttaccagca ttatcataaa    1800
gagtgatacg ttttatcttt tttatttccc agatctcggc tggagagct gtattgagca     1860 tgtatggaag gatactgtcg tgtaccttga ccgtaacaag ccgataatga ttggccgagc    1920
atatggccgg gtggaccgag acttgctgca cgaggagttg ctgagaaggt acattctatc    1980
ataacgatct tggaattcag tcgcgtcagg cagcatcata tatatgattg ttcctagtaa    2040
tgataattaa acaattggca gatgcaatga agctggtgtt acatacctca actcaaaggt    2100
tgaacagata aagaatctc ctgatggaca tcgagtagta tattgtggaa ggggccacaa     2160
gatactttgc aggcttgcca ttgttgcatc tggagcagca tttggtaagc ttctagagta    2220
tgaggttgga ggaccacgtg tttgtgtgca gactgcatac ggtgtagaag tcgaggtaca    2280 caccaacccct gcacaaagtg ctccttctga ttcgtggttt atttcatgat ttgcatgtca   2340
cttcattcat gtcattcgag ctgagaaatt catatgttgt ttgtgcacca gttcaatttt    2400
tcagaatgat gtcaaaattt caggttgaaa gatatccgta cgatcccagc ttaatggttt    2460
tcatggacta cagagattgt ttcaaagaga agttcacaca ccctgaggaa gccaatccaa    2520
catttctcta tgccatggcc atgtcatcta cacgagtttt ctttgaggtc tacatgaatt    2580
tttttagcag tgtgtttctg caatggacac gtttccataa ggataggtca ctgaccaaga    2640
taatttatca taggaaacat gcttagcttc aaaagatgca atgccttttg atctccttaa    2700
gaagaggttg atgtctcggt tggatgcgat gggagttcgt atcataaaag tatacgagga    2760
ggtaacgagt ttggagttga tatccatact ggtttatctt gcacaggtgt gctgaatttc    2820
tgttgagtct tgatttcagg agtggtctta tattcctgtt ggaggatcct tacctaacac    2880
agaccagaag aatcttgcat ttggtgctgc agcgagtatg gtccatcctg caactggtac    2940
atacaaatcc tcaactttaa ctcgtcattc tttattattt gacatgcata ttgacaatat    3000
tgtagaaaat tcataggata ttcggtggtc agatctttgt ctgaagctcc tagatatgct    3060
tctgtgatat ctgatatctt acgaaatcgt gtctattctg acaatatttt gcctggaagt    3120
tctgaaatgt ccagtccatc aatgcttggt acagatttct tcccttgttc actaaattca    3180
acagatagaa taaatcact taagatgttt ttgcagaata ggagaaatga gcagaagtat     3240
ctgctgctaa ccactgtctg atatttcagc atggggaaca ctatggcctc aagaacggaa    3300
acgtcagcgc tcattcttcc tctttggatt ggccttgata attcaactgg ataacgaagg    3360
cattcaaaca ttcttcgaga gcttttttccg gttacccaaa tggtaattat gcccgctcga    3420
tgcatttact gcttgttttc aggccctgga ccaagtattt cctttttcgc gaatacaata    3480
cgcaaggatg cgtatctttc cattgacaga aaaagtttga acaagtaaat atttccttgc    3540
gcgtgacttt tgatggatcg atctcttgaa caggatgtgg cgaggattcc ttggttcgac    3600
gctttcgtca gcggatctca tgctgtttgc actctacatg tttgcaattg cgccaaacac    3660
tttgcgaatg aacctcgtca gacacctcct ctcggacccg actggttcgg caatgatcag    3720
gacctacctg accttgtaa                                                 3739
```

<210> SEQ ID NO 3

```
<211> LENGTH: 22
<212> TYPE: DNA
<213> ORGANISM: Artificial Sequence
<220> FEATURE:
<223> OTHER INFORMATION: A3F-A7R-F

<400> SEQUENCE: 3
ccacagtagc aaaaattagt ca                                              22

<210> SEQ ID NO 4
<211> LENGTH: 22
<212> TYPE: DNA
<213> ORGANISM: Artificial Sequence
<220> FEATURE:
<223> OTHER INFORMATION: A3F-A7R-R

<400> SEQUENCE: 4
tgctacattt cacagtggtg aa                                              22

<210> SEQ ID NO 5
<211> LENGTH: 22
<212> TYPE: DNA
<213> ORGANISM: Artificial Sequence
<220> FEATURE:
<223> OTHER INFORMATION: A8F-A9R-F

<400> SEQUENCE: 5
ggttgaaaga tatccgtaca ac                                              22

<210> SEQ ID NO 6
<211> LENGTH: 22
<212> TYPE: DNA
<213> ORGANISM: Artificial Sequence
<220> FEATURE:
<223> OTHER INFORMATION: A8F-A9R-R

<400> SEQUENCE: 6
tttgggtaac cggaaaaagg tt                                              22

<210> SEQ ID NO 7
<211> LENGTH: 22
<212> TYPE: DNA
<213> ORGANISM: Artificial Sequence
<220> FEATURE:
<223> OTHER INFORMATION: B4F-B6R-F

<400> SEQUENCE: 7
caccaaccct gcacaaagtg cc                                              22

<210> SEQ ID NO 8
<211> LENGTH: 22
<212> TYPE: DNA
<213> ORGANISM: Artificial Sequence
<220> FEATURE:
<223> OTHER INFORMATION: B4F-B6R-R

<400> SEQUENCE: 8
ggaatataag accactcctg ag                                              22

<210> SEQ ID NO 9
<211> LENGTH: 22
<212> TYPE: DNA
<213> ORGANISM: Artificial Sequence
<220> FEATURE:
<223> OTHER INFORMATION: D2F-D5R-F

<400> SEQUENCE: 9
```
gctgagaagg tacattctat ca                                               22

<210> SEQ ID NO 10
<211> LENGTH: 22
<212> TYPE: DNA
<213> ORGANISM: Artificial Sequence
<220> FEATURE:
<223> OTHER INFORMATION: D2F-D5R-R

<400> SEQUENCE: 10
ttgaactggt gcacaaacaa ca                                               22

<210> SEQ ID NO 11
<211> LENGTH: 22
<212> TYPE: DNA
<213> ORGANISM: Artificial Sequence
<220> FEATURE:
<223> OTHER INFORMATION: Lcye-all-F2

<400> SEQUENCE: 11
tgaccacyga atatccagtt gc                                               22

<210> SEQ ID NO 12
<211> LENGTH: 22
<212> TYPE: DNA
<213> ORGANISM: Artificial Sequence
<220> FEATURE:
<223> OTHER INFORMATION: Lcye-all-R6

<400> SEQUENCE: 12
agttttcttt gaggaaacat gc                                               22

<210> SEQ ID NO 13
<211> LENGTH: 22
<212> TYPE: DNA
<213> ORGANISM: Artificial Sequence
<220> FEATURE:
<223> OTHER INFORMATION: Lcye-A1-F7

<400> SEQUENCE: 13
gttgctgaga agatgcaacg at                                               22

<210> SEQ ID NO 14
<211> LENGTH: 22
<212> TYPE: DNA
<213> ORGANISM: Artificial Sequence
<220> FEATURE:
<223> OTHER INFORMATION: Lcye-A1-R7

<400> SEQUENCE: 14
caaagtatct tgcggtccct tt                                               22

<210> SEQ ID NO 15
<211> LENGTH: 22
<212> TYPE: DNA
<213> ORGANISM: Artificial Sequence
<220> FEATURE:
<223> OTHER INFORMATION: Lcye-B1-F3

<400> SEQUENCE: 15
atctccagat ggacatcgag tg                                               22

<210> SEQ ID NO 16
<211> LENGTH: 22
<212> TYPE: DNA

```
<213> ORGANISM: Artificial Sequence
<220> FEATURE:
<223> OTHER INFORMATION: Lcye-B1-R3

<400> SEQUENCE: 16
tccaacctca tactctagaa gt                                              22

<210> SEQ ID NO 17
<211> LENGTH: 20
<212> TYPE: DNA
<213> ORGANISM: Artificial Sequence
<220> FEATURE:
<223> OTHER INFORMATION: Lcye-D1-F3

<400> SEQUENCE: 17
ttggccctga tcttccattc                                                 20

<210> SEQ ID NO 18
<211> LENGTH: 22
<212> TYPE: DNA
<213> ORGANISM: Artificial Sequence
<220> FEATURE:
<223> OTHER INFORMATION: Lcye-D1-R1

<400> SEQUENCE: 18
atatactact cgatgtccat ca                                              22

<210> SEQ ID NO 19
<211> LENGTH: 20
<212> TYPE: DNA
<213> ORGANISM: Artificial Sequence
<220> FEATURE:
<223> OTHER INFORMATION: Actin-F

<400> SEQUENCE: 19
ctgatcgcat gagcaaagag                                                 20

<210> SEQ ID NO 20
<211> LENGTH: 20
<212> TYPE: DNA
<213> ORGANISM: Artificial Sequence
<220> FEATURE:
<223> OTHER INFORMATION: Actin-R

<400> SEQUENCE: 20
ccaccgatcc agacactgta                                                 20
```